United States Patent [19]

Ax et al.

[11] Patent Number: 4,772,554

[45] Date of Patent: Sep. 20, 1988

[54] OVA FERTILIZATION ASSAY

[75] Inventors: Roy L. Ax; Mary E. Bellin, both of Mazomanie, Wis.

[73] Assignee: Wisconsin Alumni Research Foundation, Madison, Wis.

[21] Appl. No.: 694,437

[22] Filed: Jan. 24, 1985

[51] Int. Cl.[4] .................. C12Q 1/38; G01N 33/48
[52] U.S. Cl. ......................... 435/23; 435/4; 435/24; 436/63; 436/65
[58] Field of Search ............. 435/4, 23; 436/63, 65

[56] References Cited

PUBLICATIONS

Bellin et al–Endocrinology, vol. 114, (1984), pp. 428–433.
Grimek et al–Biochem. & Biophys. Research Communications, vol. 104, No. 4, (1982), 1401–1406.
Ax et al–Biol. of Reproduction, vol. 20, (1979), pp. 1123–1132.

*Primary Examiner*—Sam Rosen
*Attorney, Agent, or Firm*—David J. Houser

[57] ABSTRACT

A method for assaying the fertilization potential of a mammalian ovum that has been removed from an ovarian follicle, together with a portion of accompanying follicular fluid. The method includes the step of measuring the concentration of at least one selected glycosaminoglycan in the follicular fluid accompanying the ovum to be tested. That concentration is then compared with concentrations of the same glycosaminoglycan characteristic of the follicular fluid of atretic and non-atretic follicles.

10 Claims, 2 Drawing Sheets

OVA FERTILIZATION ASSAY

TECHNICAL FIELD

The present invention relates to in vitro fertilization of ova in general and, in particular, to the evaluation of the potential ability of ova to be fertilized.

BACKGROUND OF ART

The in vitro fertilization of ova is undertaken in a variety of contexts. In human beings, a woman typically is treated with follicle stimulating hormone or is otherwise so treated as to stimulate superovulation. As a consequence, the numbers of follicles that are large and have the appearance of being ready to release an ovum at the proper time in the menstral cycle are increased. In any event, at the appropriate time the contents of at least some of the large follicles in the woman's ovaries are gently aspirated to remove the ova from the follicles, together with some of the follicular fluid in which they had been bathed. When it is desired to induce the woman to conceive, the ova are exposed to sperm in vitro and the resulting embryos are returned to the woman's uterus, where it is hoped implantation will occur and a pregnancy result.

An ovarian follicle is a constantly changing structure as it develops toward the point at which it may release an ovum. At any given point in that development, the ovarian follicle may become atretic. An atretic follicle subsides and eventually is entirely readsorbed within the tissue of the ovary, with no ovulation of the ovum. Ovarian follicles may be of any size at the point at which they become atretic. Thus, it is possible and in fact is normal for many follicles that are nearly at the point of releasing an ovum to become atretic. Without intervention, even such follicles as these subside with no release of a fertilizable ovum.

The change by which a follicle shifts from a developing follicle destined to release an ovum to an atretic follicle is an event not marked by an immediate visual change. Nevertheless, an ovum even if from a follicle that has only recently become atretic is unlikely to be fertilized when exposed to sperm. Thus, when several ova are removed from the ovaries of a woman, it is not possible by a visual examination to determine if a particular ovum was taken from a healthy follicle and is likely to undergo fertilization or if it is from an atretic follicle. As a partial consequence, when in vitro fertilization is being utilized as a means of obtaining a pregnancy in a woman, it is common procedure to remove several ova from the follicles of the woman, to attempt to fertilize them all, and then to return all of them to the woman's uterus.

The difficulty of reliably predicting the fertilizability of any given human ovum presents special problems because of ethical considerations. There is evidence suggesting that the ideal number of fertilized ova to be returned to a woman in order to achieve a pregnancy is approximately four. However, in many instances, as many as ten or more ova are harvested from the ovaries of a single woman. There is no simple and convenient conventional method by which it is possible to determine which ova out of the ten or more so removed are most likely to be capable of development. Available methods require expensive machinery, the employment of persons of high skill, and the use of radioactive substances.

In practice, it is common to attempt to fertilize all of the ova that have been removed from the ovaries. With all of the ova fertilized, the ethical need arises to reimplant all of them. It is deemed ethically repugnant to discard potentially viable, fertilized ova. But the result of reimplanting an increased number of ova is a reduced chance of ultimate success in achieving pregnancy.

It would be better to be able to discern those ova having a high probability of potential fertilization, to fertilize only them, and to implant only them. Ethical tensions would be reduced in that no fertilized ova would be abandoned. At the same time chances for a successful pregnancy would be increased by the use of the ova most likely to succeed in the numbers that have been shown to provide the best chance of success. It should be noted that, for reasons not clearly understood, it is most common that only one of the fertilized ova successfully implants and proceeds to develop, regardless of the number of ova reintroduced into the woman after fertilization.

In vitro fertilization is also used for purposes other than attempting to achieve pregnancy in humans. For example, in vitro fertilization has been used to achieve a bovine pregnancy. In addition, it is important to the bovine artificial insemination industry to assess the fertility of its bulls. Traditionally this has been done by attempting to fertilize large numbers of cows, carefully preserving data relating to numbers of inseminations necessary to achieve a pregnancy. A faster and less expensive alternative to this method is to collect large numbers of bovine ova at slaughter and attempt in vitro fertilization of the ova with semen taken from the bull to be tested. By this means, tests of the bull's ability to fertilize hundreds of ova may be completed in a few days' time at minimal cost and without putting valuable cows at risk. However, the results of such tests are suspect unless it can be determined if the ova to be used are themselves capable of being fertilized. As in the case of humans, discussed above, bovine ova from atretic follicles are unlikely to be fertilized in vitro, even by semen from the most fertile bull. It is not unusual for ova from atretic follicles to account for a third, a half, or even more of the ova harvested from an ovary. While it can be predicted that some of the ova will be from atretic follicles, it cannot be predicted, especially in relatively small samples, how many will be from atretic follicles. Consequently, the method of testing for bull fertility referred to remains inherently inaccurate without knowledge of the nature of the follicles from which ova used in the test have been taken.

Those skilled in the art are cognizant of methods for predicting the success of attempts to fertilize an ovum taken from a human follicle. The conventional method known to those skilled in the art involves an analysis of the follicular fluid in which the ovum has been bathed. See Ronald S. Carson et al., "Successful Fertilization of Human Oocytes in vitro: Concentration of Estradiol-17 beta, Progesterone, and Androstenedione in the Antral Fluid of Donor Follicles" (1982), *J. Clin. Endocrinol. Metab.*, 55, 798-800. The method referred to involves a determination of the concentration of one or more of the steroids mentioned in the title of the article by Carson, et al. in fluid taken from human ovarian follicles from which ova have been aspirated. High concentrations of estradiol-17 beta are associated to a statistically significant extent with the achievement of fertilization in vitro, subsequent normal embryo growth, and pregnancy. High concentrations of progesterone also significantly correlate with successful in vitro fertilization and normal embryo growth. High concentrations of androstenedione are not predictive of successful in vitro fertilization but are predictive of normal embryo growth and subsequent pregnancy.

The concentrations of these steroids in the follicular fluid are very low, making analysis for them difficult. Typically, as in the article by Carson, et al. referred to above, concentrations must be determined by specific radioimmuno assays. A high degree of skill is involved in conducting such assays. The necessary equipment is expensive, and the facility undertaking the assay must be equipped and licensed to work with radio isotopes. As a consequence of all of these difficulties, analysis of follicular fluid for the steroids as a means for predicting the fertilizability of an ova has generally been limited to experimental situations or, in some instances, to human application in sophisticated medical facilities. The method is not available in realistic terms to the bovine artificial insemination industry, which has no commercially practical method for determining ova fertilizability. Likewise, many research facilities that are not equipped or licensed to undertake radioimmuno assays are cut off from research involving ova fertilizability.

BRIEF SUMMARY OF THE INVENTION

The method of the invention is summarized in that a method for assaying the fertilizability of a mammalian ovum to be tested that has been removed from a ovarian follicle, together with a portion of accompanying follicular fluid, includes the step of measuring the concentration of at least one selected glycosaminoglycan in the follicular fluid accompanying the ovum to be tested. That concentration is then compared with concentrations of the same glycosaminoglycan characteristic of the follicular fluid of atretic and non-atretic follicles.

The kit of the invention is summarized in that a kit for the convenient measurement of glycosaminoglycan concentrations in mammalian follicular fluid includes means to supply nitrous acid. The kit further includes means to supply aqueous solutions of a spectrophotometrically measurable, water soluble complexing agent, sodium doecyl sulfate, and gelatin.

A primary object of the invention is to provide an indicator of atresia in ovarian follicles and therefore a means to evaluate the fertilizing potential of ova taken therefrom.

Another object of the invention is to provide such methods of indicating atresia and evaluating the fertilizing potential of ova that may be undertaken at modest expense and by workers of modest skill.

A further object of the invention is to provide such methods suitable for commercial application in the artificial insemination industry.

A further object of the invention is to provide a spectrophotometric method of indicating atresia in ovarian follicles and thus evaluating the fertilizability of an ovum taken from such a follicle.

Yet another object of the invention is to provide methods such that atresia and the fertilizability of ovum may be evaluated quickly.

A further object of the invention is to provide a kit for the convenient exercise of the methods.

Other objects, features, and advantages of the invention will be apparent from the following detailed description taken in conjunction with the accompanying drawings.

BRIEF DESCRIPTION OF THE DRAWINGS

The drawings are graphs presenting data identified in full in the following Detailed Description of the Preferred Embodiment.

DETAILED DESCRIPTION OF THE PREFERRED EMBODIMENT

Figure 1:
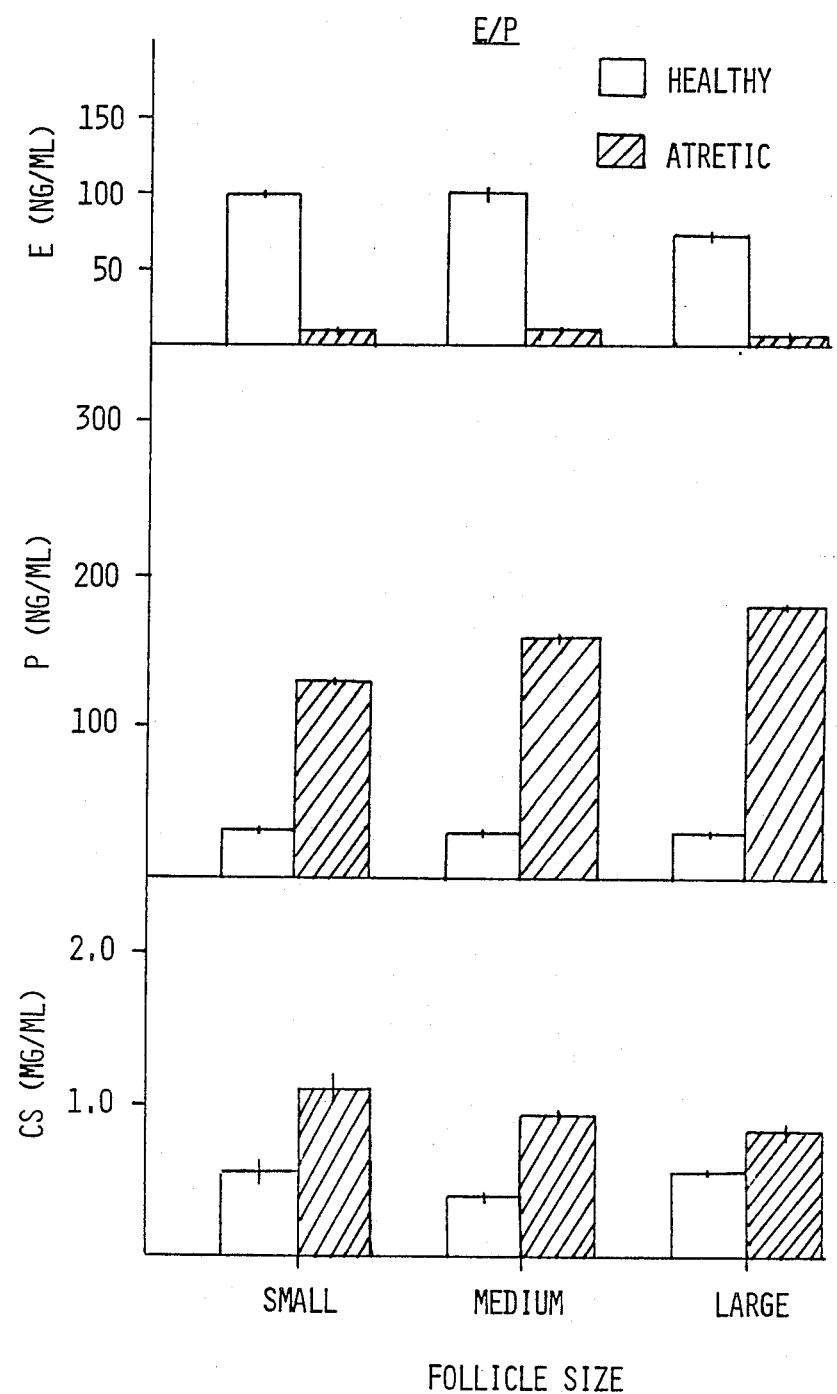

In general terms, the method of the invention for assaying ova fertilizability in mammals includes utilizing a selected assay to measure the concentration of glycosaminoglycans (hereinafter GAGs) in follicular fluid. GAG concentrations are related to the status of the follicle as atretic or non-atretic and to the fertilizability of the ovum contained within the follicle. As is noted above, those skilled in the art are aware of the relationship between both the concentration of estrogen and the ratio of estrogen to progesterone in the follicular fluid to the chances for recovery of an ovum, its fertilization in vitro, the normal growth of an embryo therefrom, and a resulting pregnancy. In the paper referred to above, Carson, et al. report a positive correlation between high concentrations of estrogen (and between high ratios of estrogen to progesterone) and the chances for successful fertilization, embryo growth, and pregnancy in humans.

In the work reported as Example 1, below, it has now been discovered that the concentration of certain GAGs in a sample of follicular fluid is reliably related to the concentrations of estrogen and progesterone and therefore also may be used as an indicator of a follicle's healthy or atretic condition. Healthy and atretic follicles of bovine ovaries were compared, and it was verified that healthy follicles are characterized by concentrations of estrogen that are high relative to the concentrations of estrogen in atretic follicles, and that the concentrations of estrogen and progesterone are significantly negatively correlated. It was also discovered, however, that the concentration of the GAG chondroitin sulfate (hereinafter CS) is predictively related to the concentrations of estrogen and progesterone. The concentration of estrogen versus that of CS was significantly negatively correlated, whereas a significant positive correlation existed between the concentrations of progesterone and CS.

For a variety of reasons, it is much easier to measure concentrations of CS in follicular fluid than concentrations of either progesterone or estrogen. For example, CS concentrations in follicular fluid are commonly in the range of 0.3 to 1.2 mg/ml. In contrast, typical progesterone concentrations are on the order of 25 to 180 ng/ml. Estrogen concentrations are on the order of 10 to 100 ng/ml. As a consequence, while estrogen and progesterone assays typically must employ radioimmunoassay techniques, concentrations of CS on the order referred to may be determined by gel filtration using high pressure liquid chromatography or by spectrophotometric means such as those disclosed by Paul Whiteman in "The Quantitative Measurement of Alcian Blue-Glycosaminoglycan Complexes" (1973), *Biochem. J.*, 131, 343–350; and Paul Whiteman, "The Quantitative Determination of Glycosaminoglycans in Urine with Alcian Blue 8GX" (1973), *Biochem. J.*, 131, 351–357.

Other methods of quantitative measurement of CS and of heparan sulfate are well known in the art, including but not limited to those discussed by Whiteman in the two articles referred to. For examples, see R. B. Cundall and D. Murray, "Spectrofluorimetric Methods for Estimating and Studying the Interactions of Polysaccharides in Biological Systems" (1978), in *Carbohydrate Sulfates*, ed. Richard G. Schweiger, ACS Symposium Series, 77, American Chemical Society, pp. 67–94; and Yan-Yu Wu and Margo Panush Coben, "A Competitive Binding Assay for Measurement of Heparan Sulfate in Tissue Digests" (1984), Anal. Biochem., 139, 218–223. The alcian blue assay method described by Whiteman was developed and has been used predominantly for the measurement of GAGs in urine for diagnostic and other purposes.

In the experiments reported as Example 2, below, it has been discovered that concentrations of the GAGs CS and heparan sulfate (HS) can be correlated with maturation, pronuclear formation, and cleavage in oocytes in human beings. Pronuclear formation was found to be significantly higher when CS quantities were low. Maturation scores for a visual assessment of the egg-corona-cumulus-cell complexes increased, whereas pronuclear development decreased, as HS levels increased. In general, it was found that pronuclear formation was higher when total GAG concentration was low, for example below 1 mg/ml. Thus it is apparent that CS concentrations bear not only a predictable relationship to progesterone and estrogen concentrations but also to oocyte developmental competence. It is preferred in the method of the invention to remove the HS and HS-like compounds from the follicular fluid prior to measuring CS concentration. This can be accomplished by treating the follicular fluid with nitrous acid.

Finally, in work presented as Example 3, below, the ability of a spectrophotometric assay method generally similar to the alcian blue complex method described by Whiteman to measure GAGs concentrations sufficiently accurately to serve as an indicator of ova fertilizability was tested against the results obtainable by high pressure liquid chromatography. Initial exposure of the follicular fluid to nonspecific proteases of sorts well known in the art was found to increase the sensitivity of the alcian blue assay. It was discovered that the results of the spectrophotometric assay method agreed well with the results obtained by hiqh pressure liquid chromatography in those GAG concentration ranges associated with a high degree of ova fertilizability.

EXAMPLE 1

Comparison of Concentrations of CS, Estrogen, and Progesterone in Bovine Follicular Fluid Bovine ovaries from 201 cows were obtained from Oscar Mayer and Company, Madison, Wis. 30 minutes of slaughter. Follicular fluid was aspirated from a total of 638 follicles by needle and syringe and was frozen on dry ice. The follicular fluid was stored at −20° C. until required for assays. The follicles aspirated were classified as small, medium, and large follicles having diameters of 5 mm or less, 6 to 10 mm, and 11 to 20 mm, respectively. Concentrations of estrogen, progesterone, and CS were assayed in the samples in the following ways:

CS Assay: CS was isolated from 10 microliter portions of follicular fluid and precipitated with alcohol after digestion with protease, following the method set forth in R. L. Ax and R. J. Ryan (1979), "The Porcine Follicle. IV. Mucopolysaccharides at Different Stages of Development," Biol. Reprod., 20, 1123. Concentrations of CS were then determined by gel filtration using high pressure liquid chromatography, integrated areas of peaks being compared to standards after the method of H. J. Grimek and R. L. Ax (1982), "Chromatographic Comparisons of Chondroitin-Containing Proteoglycan from Small and Large Bovine Ovarian Follicles," Biochem. Biophys. Res. Commun., 104, 1401. Absorbance was monitored at 205 nm.

Estrogen Assay: An immunoradio-assay for estrogen was employed that had previously been validated for follicular fluid by E. A. Merz, et al. (1981), "Ovarian Function in the Cycling Cow; Relationship between Gonadotropin Binding to Theca and Granulosa and Steroidogenesis in Individual Follicles," *J. Anim. Sci.*, 52, 1457. Estrogen was extracted from 10 microliter samples of follicular fluid with 0.5 ml anesthetic grade diethyl ether. The tracer hormone used was 17beta-[2,4,6,7,16,17,—(N)—$^3$H] estradiol obtained from New England Nuclear Corp., Boston, Mass.; SA, 137.0 Ci/mmol). The specificity of the estrogen antisera had been characterized previously by B. England, et al. (1974), "Radioimmunoassay of Estradiol 17 beta without Chromatography," *J. Clin. Endrocrinol. Metab.*, 38, 42. The inter- and intraassay coefficients of variation were 4.4% and 4.5% respectively. The sensitivity of the assay was $24.2 \pm 1.7$ mg/ml (mean±SEM; n=7).

Progesterone Assay. An immunoradio-assay for progesterone was employed, as described in C. N. Lee (1981), "Gonadotropin Releasing Hormone: Its Possible Usage in the Management of Dairy Heifers and Postpartum Cows," M. S. Thesis, University of Wisconsin, Madison. In that assay, progesterone was extracted from 10 microliter samples of follicular fluid with 0.5 ml petroleum ether. The tracer hormone used was [1, 2, 6, 7, 7—(N)—$^3$H]P obtained from New England Nuclear; SA, 101.0 Ci/mmol. The sensitivity of the assay was calculated to be $27.14 \pm 5.1$ mg/ml (mean±SEM). The progesterone antibody cross-reacted with 5 alpha-dihydroprogesterone (3.1%), 17 alpha-, 20 alpha-, and 20 beta-hydroxyprogesterone (10.2%, 2.8%, 1.5%, respectively); and deoxycorticosterone (2.83%). The respective interassay coefficients of variation were 4.3%, 9.7%, and 21.2% at doses of 125, 500, and 2000 mg (n=50).

The immunoradio-assays were performed using sufficient labeled steroid to obtain a count rate of 60,000 dpm for each tube containing the estrogen or progesterone extracted from the 10 microliter follicular fluid sample. Estrogen and progesterone antisera were diluted 1:5000 and 1:1000, respectively, to bind approximately 50% of the labeled steroid. Bound and free steroids were separated by the dextran-coated charcoal technique. The supernatant and 4.0 ml 3a70b scintillation cocktail (Research Products International, Madison, Wis.) were pipetted into miniscintillation vials, and radioactivity was monitored in a Beckman liquid scintillation spectrophotometer obtained from Beckman Instruments, Palo Alto, Calif.

For each follicle size, follicles were classified as healthy or atretic if their estrogen concentrations were equal to or in excess of one standard deviation above or below the mean estrogen concentration, respectively. Estrogen concentrations were such that small, medium, and large follicles having estrogen levels greater than 40.7, 47.9, and 58.9 ng/ml respectively were classified as healthy. Such follicles having estrogen levels less than 2.9, 2.6, and 2.3 ng/ml, respectively, were classified as atretic. Such classification of follicles by estrogen level shall be referred to hereinafter as the concentration of estrogen method of classification. In addition, follicle health was independently classified by histological examination and by calculation of the estrogen to progesterone concentration ratio for each follicle. The classification systems used are reported in M. E. Bellin and R. L. Ax (1984), "Chondroitin Sulfate: An Indicator of Atresia in Bovine Follicles," *Endocrinology*, 114, 428–434.

The relationship of concentrations of estrogen, progesterone, and CS did not change among the classifications of follicle health by all three methods of classification. Estrogen concentrations were significantly greater in healthy follicles at all follicle sizes. Progesterone concentrations were significantly elevated in atretic follicles. CS concentrations were greater in atretic follicles than in healthy follicles, and this relationship was significant when the estrogen concentration and the estrogen to progesterone concentration methods were used to classify follicle health. FIG. 1 sets forth the concentrations of estrogen, progesterone, and CS (mean±SEM) for healthy and atretic follicles (identified as healthy or atretic by the concentration of estrogen method) for each follicle size. CS concentration proved to be negatively correlated to estrogen concentration and positively correlated to progesterone concentration. Those relationships were reliable, consistent, and statistically significant for follicles regardless of follicle size. Statistical analysis and a discussion of CS concentration relative to estrogen and progesterone concentrations in follicles classified by the other health classification methods are all set forth in full in the article by Bellin and Ax just referred to.

The results set forth in this example clearly establish that there is a predictable and perceivable relationship between CS concentration and both estrogen and progesterone concentrations in bovine follicles of small, medium, and large sizes. It is already accepted in the art that there is a significant relationship between estrogen concentrations and both atresia and ovum fertilizability. Consequently, the example shows that the concentration of CS may be used as an indicator of the healthly or atretic status of bovine follicles and the fertilizability of ova recovered therefrom.

EXAMPLE 2

Concentration of CS and Heparan Sulfate (hereinafter HS) Correlated with Maturation, Pronuclear Formation, and Cleavage of Oocytes in Humans 178 samples of human follicular fluid were obtained from Dr. Florence P. Haseltine of the Yale University School of Medicine, New Haven, Conn. The samples of follicular fluid had been aspirated from follicles of women attempting to achieve a pregnancy by means of in vitro fertilization of their ova. In many instances, more than one follicle was aspirated in a particular woman, so that the 178 samples of follicular fluid represent samples from 105 women. All of the follicles taken were large follicles relative to the remaining ovarian follicles.

With records being kept follicle by follicle, ova were evaluated for maturity microscopically. After in vitro fertilization, the development of pronuclei and cleavage were also observed microscopically. Because all of the fertilized ova taken from any given woman were returned to her uterus for implantation, it became impossible to determine which ovum coming from which follicle resulted in a pregnancy. Nevertheless, when a pregnancy occurred, it was possible to state that the pregnancy resulted from an ovum taken from one of several particular follicles.

Concentrations of CS and HS were assayed by high pressure liquid chromatography after selective degradation of the other class of GAGs, generally in accord with the method for assaying CS described in Example 1. CS and HS concentrations ranged from 0 to 3.9 and 0 to 18.0 mg/ml, respectively.

Figure 2:
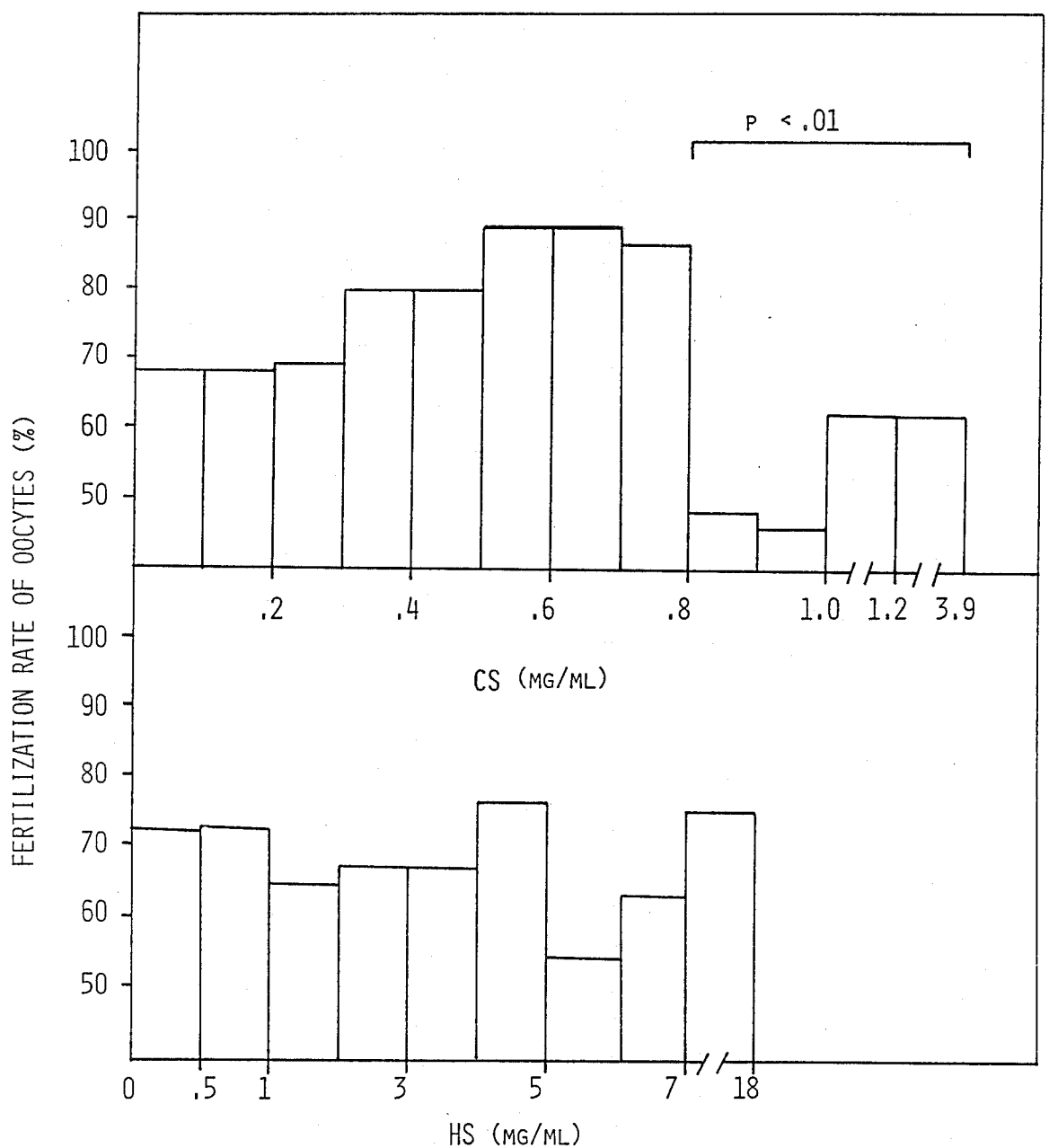

Analysis of variance was used to relate maturation, pronuclear formation, and cleavage of oocytes to CS and HS concentrations. The results showed that pronuclear formation was significantly higher when the CS quantities ranged from 0.3 to 0.8 mg/ml. Rates of fertilization were 67.8, 84.2 and 57.3% when CS concentrations ranged from 0 to 0.3, 0.3, to 0.8 and 0.8 to 0.39 mg/ml follicular fluid, respectively. Maturation scores for visual assessment of the egg-corona-cumulus-cell complexes increased, whereas pronuclear development was not affected, as HS levels increased ($p<0.05$). In general, pronuclear formation was higher when total GAG concentration was less than 1 mg/ml in the follicular fluid. The results are set forth in FIG. 2, wherein the percentage of ova fertilized for each concentration of CS and HS is shown. A high pronuclei count per egg is indicative of viable ova that have been successfully fertilized, with increased chances for production of a successful pregnancy upon reinsertion into the woman. Thus, the results disclosed show that ova taken from follicles the fluid of which contains CS in a quantity ranging from 0.3 to 0.8 mg/ml are significantly more likely to be viable and to be successfully fertilized in vitro. Consequently, an increased chance exists for a successful pregnancy when such ova are selected for reimplantation within the woman. Likewise, ova taken from follicles the fluid of which exhibits a total GAG concentration less than 1 mg/ml are more likely to be successfully fertilized in vitro and to exhibit successful pronuclear formation, desirable cleavage rates, and elevated chances for resulting in a pregnancy.

EXAMPLE 3

Measurement of GAGs in Bovine Follicular Fluid Using Alcian Blue Dye.

Alcian blue 8GX was used to quantitatively measure by a spectrophotometric procedure the concentration of GAGs in bovine follicular fluid.

CS standards ranging from 0–25 micrograms, as well as the same CS standards spiked with 10 microliters of fluid pooled from large bovine follicles having external diameters of 11 to 20 mm, were assayed concurrently in duplicate. Each sample to be assayed was placed in an assay tube. Alcian blue reagent (0.05% w/v) was prepared containing 50 mM magnesium chloride and 50 mM sodium acetate and adjusted to pH 5.8 with glacial acetic acid. 1 ml of the alcian blue reagent was added to each assay tube. The tubes were then placed in a 37° C. shaking water bath for 30 minutes in order to allow alcian blue-GAG complexes to be formed. The alcian blue complexes then were pelleted by centrifugation. The pellets were washed with 2 ml of 95% ethanol and recentrifuged. The supernatant fluid was decanted, and 1 ml of sodium dodecyl sulfate (0.5% w/v) was added to resuspend and dissociate the pelleted complexes. Following an additional 30 minutes in a 37° C. shaking water bath, 2 ml of gelatin (0.1% w/v) were pipetted into each assay tube. Absorbance was then monitored at 620 nm.

The assay was repeated nine times, with the following results, which are reported as mean±standard deviation. The sensitivity of the alcian blue assay was 1.2±0.6 micrograms CS. precision at CS doses of 3, 12.5, and 25 mg was 6.0% ±5.4%, 3.2% ±2.8%, and 2.8% ±2.9%, respectively. The inter-assay coefficient of variation was 5.54%. The slopes (OD units/microgram CS) of the regression lines for the CS standards (0.043±0.001) and the spiked CS standards (0.040±0.001) were substantially identical. The assay failed to detect GAG after treatment of CS and heparin with chondroitinase ABC and nitrous acid, respectively.

The method of this example was used to assay for CS and total GAG concentration in human follicular fluid, and the results were compared with assay results by high pressure liquid chromatography conducted in the manner set forth in Example 2. The alcian blue spectrophotometric procedure was found to give substantially the same results as assay by high pressure liquid chromatography for relatively low CS and GAG concentrations. However, at increased concentrations of CS and of total GAGs, as indicated by the spectrophotometric assay procedure, assay by high pressure liquid chromatography occasionally indicated that in fact the concentrations were lower than indicated by the alcian blue spectrophotometric procedure.

As a consequence of the comparisons of assay results set forth above, it has now been discovered that when a desirably low concentration of CS or total GAGs in follicular fluid is indicated by assay by the spectrophotometric procedure, those results reliably reflect actual concentrations and may be used to predict an elevated likelihood of ova viability, successful in vitro fertilization, and achievement of a pregnancy upon reinsertion of the fertilized ova in a female. In contrast, results from the spectrophotometric assay indicating high CS or total GAG concentration are not as reliable predictors of lack of ova viability, and so forth.

As an additional, optional step in the alcian blue assay set forth above, the follicular fluid may be pretreated with any nonspecific protease, such as Protease IV isolated from *Bacillus polymyxa* and available commercially from Sigma Chemical Company of St. Louis, Mo. The GAGs are not affected by this treatment, but various proteins present in the untreated follicular fluid are broken down, decreasing their ability to interfere with the assay.

The Examples given above represent particular embodiments of the method of the invention, together with information verifying the efficacy of the method of the invention. However, the invention is not limited to the particular steps, reagents, temperatures, concentrations, and the like illustrated by the examples. Instead, the method of the invention includes all alternative and equivalent forms thereof encompassed by the claims set forth below.

The kit of the invention is especially adapted for the convenient performance of the method of the invention when the step of measuring the concentration of at least one selected glycosaminoglycan in the follicular fluid accompanying the ovum to be tested is accomplished by use of a complexing agent such as alcian blue. The kit is adapted for use with a reaction vessel, such as a 12×75 test tube, which may be included as part of the kit, if desired.

The kit includes means to supply a nitrous acid. Preferably, the means to supply nitrous acid includes a supply of sodium nitrite and an aqueous solution of acetic acid. The kit further includes means to supply aqueous solutions of a spectrophotometrically measurable, water soluble complexing agent such as alcian blue, an ionic detergent such as sodium doecyl sulfate, and gelatin. If desired, a quantity of 95% ethanol may also be included in the kit. Hereinafter, alcian blue and sodium doecyl sulfate may be referred to, but only as illustrative of such complexing agents and ionic detergents, generally. The kit may also include a supply of a non-specific protease, such as Protease XV. An alternative version of the kit includes premeasured amounts of complexing agent, ionic detergent, and gelatin such that the addition of a conveniently measurable amount of water may be added thereto to create the aqueous solutions referred to. Alternatively, the ionic detergent and the gelatin may be provided as frozen aqueous solutions. Such premeasured amounts of these reagents, either with or without an accompanying supply of water, and such frozen solutions both are examples of means for supplying the reagents in aqueous solution. It is preferred that the solutions be made up with substantially pure and preferably deionized distilled water, and the kit may contain a supply of such water.

Clearly other alternative versions of the kit are possible. Thus, when a 10 microliter follicular fluid sample is to be used and the assay to be performed is for condroitin sulfate to achieve the advantages set forth above, the reaction vessel may contain a premeasured quantity of sodium nitrite, for example in the amount of 5 mg. An amount of the acetic acid solution sufficient to form the desired amount of nitrous acid may then be added to the sodium nitrite. It is preferred that the acetic acid solution be a 4N solution, in which case 0.1 ml may be added. After incubation at 25° C. for one hour, the heparin and heparan sulfate that may have been contained in the sample of follicular fluid will have been destroyed.

In the circumstances set forth in the preceding paragraph, it is preferred further that the alcian blue solution include 0.05 weight percent alcian blue 8 GX, 50 mM $MgCl_2$, and 50 mM sodium acetate. When the alcian blue solution is as described, 1 ml of that solution may be added to the sample after it has been treated with nitrous acid, and the reaction vessel may be incubated for 30 minutes, preferably in a shaking water bath at or about 37° C. and 100 oscillations per minute. After incubation, the reaction vessel is centrifuged, for example at 2000 rpm for 15 minutes, and the supernatant is discarded. 2 ml of 95% ethanol may then be added to the precipitate, which then may be agitated to distribute the precipitate therethrough. The reaction vessel may be centrifuged again at 2000 rpm for 15 minutes, and the supernatant thoroughly poured off.

Under the circumstances described, it then is preferred that the sodium doecyl sulfate solution be prepared at a concentration of approximately 0.5% by weight. One ml of a solution so prepared then may be added to the reaction vessel, and the precipitate may be agitated so as to disperse it. After incubation at approximately 37° C. for 30 minutes, the reaction vessel may be again centrifuged. It is preferred that the gelatin solution be prepared at a concentration of 0.1% by weight of gelatin. In such event, 2 ml of the gelatin solution may then be added to the centrifuged sodium doecyl sulfate solution. The supernatant so prepared then may be read in a spectrophotometer, preferably at approximately 620 nm.

If it is desired to break down protein in the follicular fluid sample with a non-specific protease, as is disclosed above, the reaction vessel may contain an appropriate amount of such protease, such as 0.01 units of Protease XV, in aqueous solution, with appropriate amounts of nitrous acid or, alternatively, sodium nitrite and acetic acid, being added to the reaction vessel after the follicular fluid sample has been incubated with the protease for approximately 30 minutes at 37° C.

It will be clear to one skilled in the art that alternative versions of the kit described above may be made, including embodiments omitting common and conveniently preserved reagents, such as 95% ethanol. However, the combination of certain reagents useful to conducting an alcian blue analysis for GAGs with other reagents useful for destroying unwanted protein or heparin and heparan sulfate results in a particular choice of reagents, assembled as a kit, that is of special utility in conducting the method of the invention.

The invention is not limited to the particular reagents or concentrations disclosed above. Instead, the kit of the invention includes all alternative and equivalent forms thereof encompassed by the claims set forth below.

What is claimed is:

1. A method for assaying the fertilizability of a mammalian ovum to be tested that has been removed from an ovarian follical, together with a portion of accompanying follicular fluid, comprising the steps of:
    (a) measuring the concentration of at least one selected glycosaminoglycan in the follicular fluid accompanying the ovum to be tested;
    (b) identifying atretic and non-atretic control follicles by identification means other than measurement of the concentration of the selected glycosaminoglycan and measuring the concentration of the selected glycosaminoglycan in the follicular fluid of the control follicles to determine the concentrations thereof characteristic respectively of atretic and non-atretic control follicles; and
    (c) comparing the concentration of the selected glycosaminoglycan in the follicular fluid accompanying the ovum to be tested with the concentration of the selected glycosaminoglycan characteristic of the follicular fluid of the atretic and non-atretic control follicles respectively, whereupon the likelihood that the ovum to be tested is fertilizable may be termed greater as the concentration of the selected glycosaminoglycan in its accompanying follicular fluid approaches that concentration that has been found to be characteristic of the follicular fluid of non-atretic control follicles and lesser as the concentration of the selected glycosaminoglycan in its accompanying follicular fluid approaches that concentration that has been found to be characteristic of the follicular fluid of atretic control follicles.

2. The method of claim 1 wherein the step of selecting control follicles identifiable as atretic and non-atretic includes assaying the follicular fluid of representative control follicles for concentration of estrogen, whereby atretic control follicles may be identified and distinguished from non-atretic control follicles as those whose follicular fluid contains a relatively low concentration of estrogen when compared with the average estrogen concentration in the follicular fluid of the control follicles while non-atretic follicles may be identified and distinguished as those whose follicular fluid contains a relatively high concentration of estrogen.

3. The method of claim 1 wherein the step of identifying control follicles as atretic and non-atretic includes assaying the follicular fluid of representative control follicles for concentration of progesterone, whereby atretic control follicles may be identified and distinguished fron non-atretic control follicles as those whose follicular fluid contains a relatively high concentration of progesterone when compared with the average concentration of the control follicles while non-atretic follicles may be identified and distinguished as those whose follicular fluid contains a relatively low concentration of progesterone.

4. The method of claim 1 wherein the glycosaminoglycan is chrondroitin sulfate.

5. The method of claim 1 wherein the step of measuring the concentration of at least one selected glycosaminoglycan in the follicular fluid accompanying the ovum to be tested includes employing a spectrophotometric assay procedure.

6. The method of claim 5 wherein the spectrophotometric procedure includes:
    (a) quantitatively combining the glycosaminoglycans with a spectrophotometrically measurable, water soluble complexing agent to form insoluble complexes therewith;
    (b) isolating the insoluble complexes from the remainder of the complexing agent;
    (c) resolubilizing the complexing agent of the insoluble complexes; and
    (d) spectrophotometrically measuring the amount of complexing agent so resolubilized.

7. The method of claim 6 wherein the complexing agent is alcian blue.

8. The method of claim 6 wherein the follicular fluid accompanying the ovum to be tested is treated with a protease prior to the step of measuring the concentration of at least one selected glycosaminoglycan therein.

9. A method for assaying the fertilizability of bovine or human ova to be tested when such an ovum has been removed from an ovarian follicle, together with a portion of accompanying follicular fluid, comprising the steps of
    (a) measuring the total concentration of all glycosaminoglycans in the follicular fluid;
    (b) selecting as having superior fertilizability ova whose follicular fluid has a total glycosaminoglycan concentration less than approximately 0.8 mg/ml; and
    (c) selecting as having inferior fertilizability ova whose follicular fluid has a total glycosaminoglycan concentration more than approximately 0.8 mg/ml.

10. A method for assaying the fertilizability of bovine or human ova when the ovum to be tested has been removed from an ovarian follicle, together with a portion of accompanying follicular fluid, comprising the steps of
    (a) measuring the concentration of chondroitin sulfate in the follicular fluid; and
    (b) selecting as having superior fertilizability ova whose follicular fluid has a chondroitin sulfate concentration greater than 0.3 mg/ml but less than 0.8 mg/ml, and selecting as having inferior fertilizability ova whose follicular fluid has a concentration of chondroitin sulfate less than 0.3 mg/ml or greater than 0.8 mg/ml.

* * * * *